US006939327B2

(12) United States Patent
Hall et al.

(10) Patent No.: US 6,939,327 B2
(45) Date of Patent: Sep. 6, 2005

(54) PEEL-AWAY SHEATH

(75) Inventors: Jeffrey A. Hall, Birmingham, AL (US);
Wade A. Bowe, Temecula, CA (US);
Bruce A. Tockman, Scandia, MN (US);
Randy W. Westlund, Minneapolis, MN (US); Neil Becker, Fallbrook, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 221 days.

(21) Appl. No.: 10/140,540

(22) Filed: May 7, 2002

(65) Prior Publication Data
US 2003/0212373 A1 Nov. 13, 2003

(51) Int. Cl.[7] .............................................. A61M 5/178
(52) U.S. Cl. .................... 604/164.05; 604/160
(58) Field of Search ............... 604/93.01, 158, 604/160–161, 163, 164.01, 164.05, 264, 523; 606/108, 129

(56) References Cited

U.S. PATENT DOCUMENTS

| | | | |
|---|---|---|---|
| 4,306,562 A | | 12/1981 | Osborne |
| 4,345,606 A | | 8/1982 | Littleford |
| 4,412,832 A | | 11/1983 | Kling et al. |
| 4,569,347 A | * | 2/1986 | Frisbie .................. 606/108 |
| 4,681,570 A | * | 7/1987 | Dalton .................. 604/524 |
| 4,936,826 A | * | 6/1990 | Amarasinghe ......... 604/507 |
| 5,104,388 A | * | 4/1992 | Quackenbush ......... 604/264 |
| 5,158,545 A | * | 10/1992 | Trudell et al. ......... 604/509 |
| 5,211,654 A | * | 5/1993 | Kaltenbach ............ 606/191 |
| 5,639,276 A | | 6/1997 | Weinstock et al. |
| 5,713,867 A | * | 2/1998 | Morris .............. 604/164.05 |
| 5,752,937 A | | 5/1998 | Otten et al. |
| 5,797,952 A | * | 8/1998 | Klein .................... 623/1.12 |
| 5,947,977 A | * | 9/1999 | Slepian et al. ........ 606/108 |
| 6,110,146 A | * | 8/2000 | Berthiaume et al. ... 604/160 |
| 6,143,016 A | | 11/2000 | Bleam et al. |
| 6,261,316 B1 | | 7/2001 | Shaolian et al. |
| 6,358,460 B1 | | 3/2002 | Hunt, Jr. et al. |
| 6,364,892 B1 | | 4/2002 | Jervis |
| 6,416,529 B1 | * | 7/2002 | Holman et al. ........ 606/194 |
| 6,443,941 B1 | * | 9/2002 | Slepian et al. ........ 604/522 |
| 2001/0049499 A1 | * | 12/2001 | Lui et al. .......... 604/164.05 |

* cited by examiner

Primary Examiner—LoAn H. Thanh
(74) Attorney, Agent, or Firm—Faegre & Benson LLP

(57) ABSTRACT

A peel-away sheath for a catheter includes at least one weakened area in a non-longitudinal pattern, such as a helical pattern, along the length of the sheath. One embodiment of a catheter sheath includes a tube having at least one pull wire integrally located within its wall. Another embodiment of a catheter sheath includes a tube having at least one integral lumen within its wall. The integral lumen may house a filling material. One embodiment of a catheter may include a first sheath which is positioned within a second sheath, with each of the first and second sheaths having at least one weakened area along its length. A reinforcing guide for a guide catheter includes a tube having a lumen with a diameter at least as large as the guide catheter diameter. The reinforcing guide includes a gap with a width which is less than the guide catheter diameter.

8 Claims, 11 Drawing Sheets

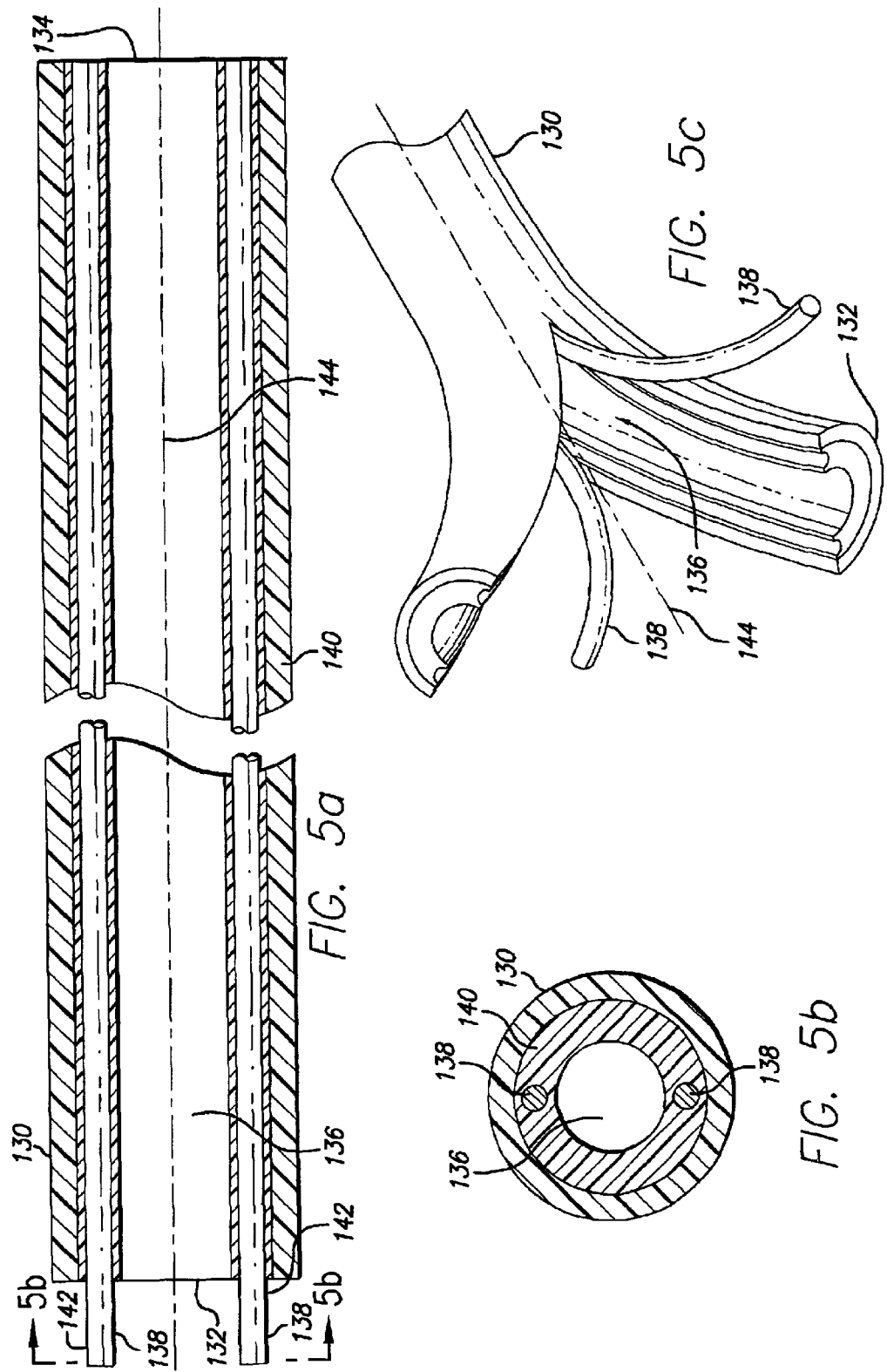

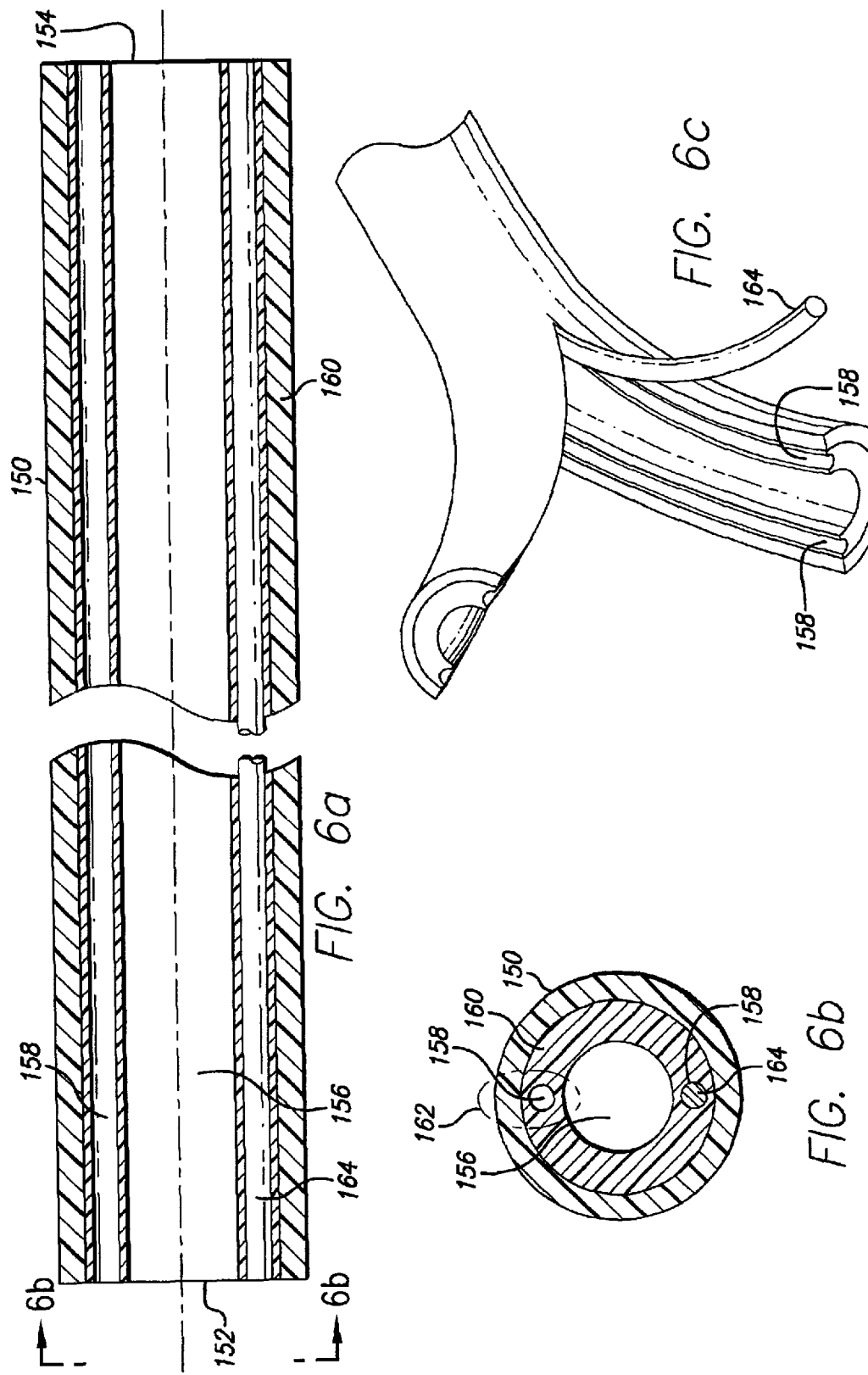

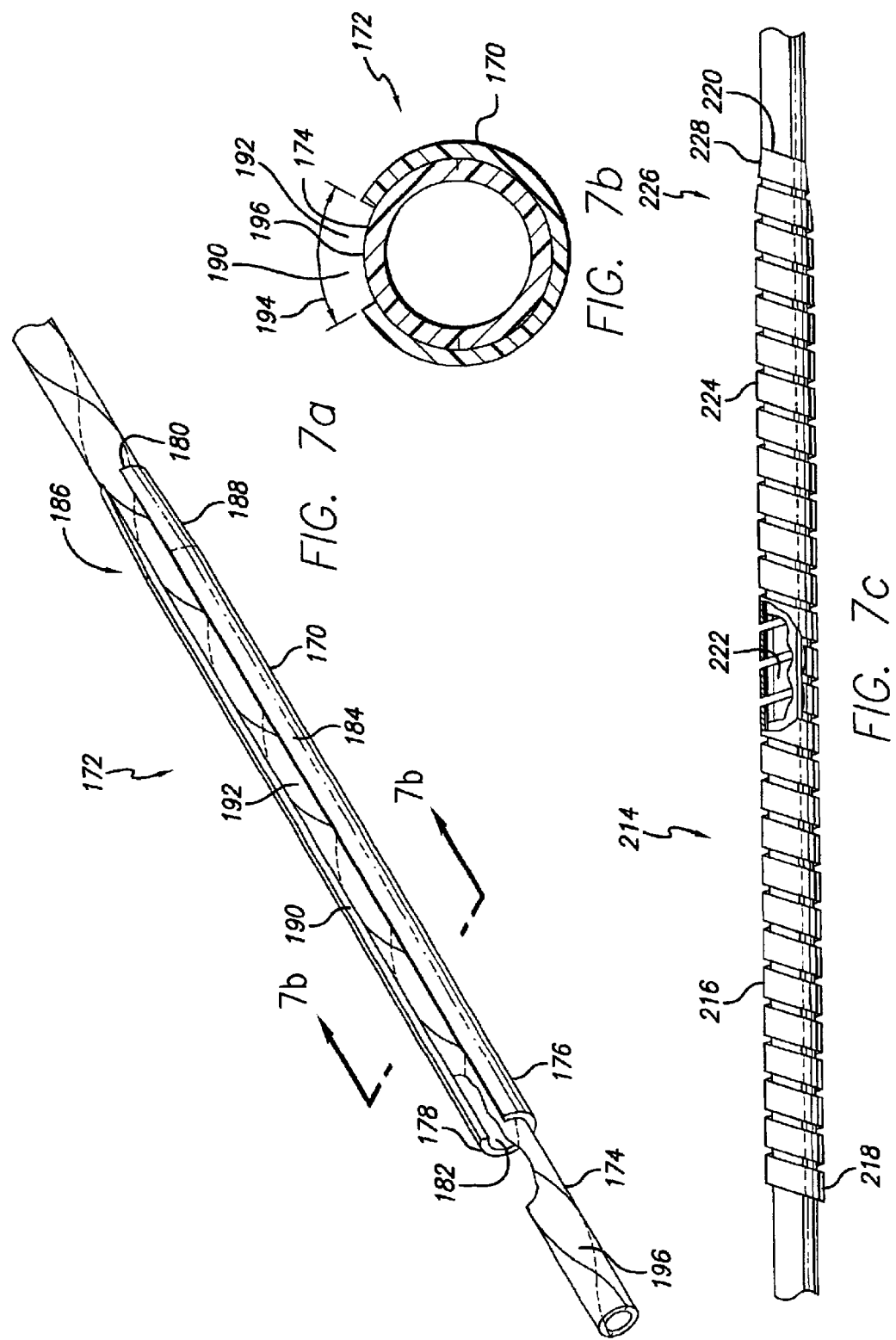

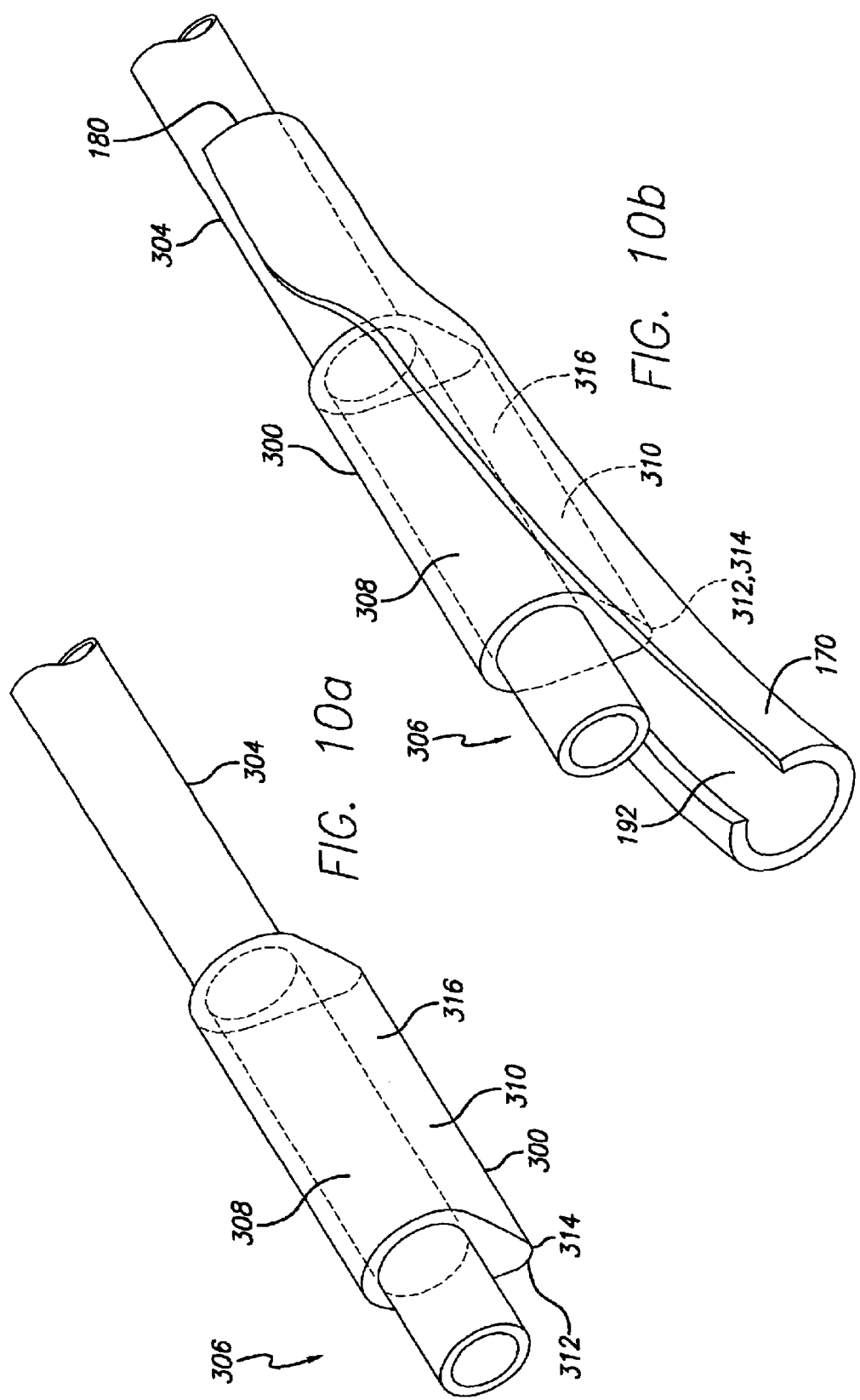

PEEL-AWAY SHEATH

BACKGROUND OF THE INVENTION

1. Field of the Invention

The invention relates generally to delivery systems for interventional devices and, more particularly, to a guiding catheter for delivering an interventional device to an anatomical site.

2. Description of the Related Art

Numerous devices and procedures have been developed for delivering interventional devices to a work site within an anatomical body. Such procedures usually involve the percutaneous introduction of an interventional device into the lumen of an artery, usually through a catheter. Some prior art devices for delivering an interventional device utilize a guiding catheter. The guiding catheter is routed through the vasculature of the anatomical body to a location proximate the work site. The interventional device which is coupled to a delivery device, such as a guide wire, is then routed through the guiding catheter and to the work site. After the interventional device is positioned at the work site, the guiding catheter is removed and the interventional device is deployed, leaving the interventional device in place. In a typical over-the-wire delivery platform the guide wire maybe more than twice the length of the delivery sheath with more than half the length external to the patient during the delivery of the interventional device. This extra length is needed when the guiding catheter is removed from the patient since the guide wire must usually be held in place. Therefore, the portion of the guide wire external the patient must be longer than the guiding catheter to allow the operator to grasp a portion of the guide wire during all stages of removal of the guiding catheter. Due to the length of the guide wire, it may sometimes be necessary to have a second person assist the operator when removing the guiding catheter to prevent the guide wire from shifting within the vessel.

Other guiding catheters include a sheath having at least one longitudinal weakened area in the form of a slit or a perforation along the length of the sheath. Other embodiments include a longitudinal groove along the length of the sheath. The purpose of the slit, groove or perforation is to provide a weakened area along the length of the sheath that can be split so that the sheath may be peeled away from the guide wire, or other delivery device, used to deliver the interventional device. Current peel-away sheaths include two longitudinal slits so that the sheath can be peeled along the slits for removal of the sheath from the guide wire or other delivery device. Guiding catheters utilizing such sheaths make it possible for the sheath to be removed from the anatomical body and the guide wire or other delivery device by just one person.

Although the longitudinal slits, grooves and perforations of current peel-away sheaths promote easy splitting of the sheaths, they also predispose the sheaths to kinking along the thinner cross sections thereby created. The longitudinal slits, grooves and perforations also make it difficult to transfer torsional loads through the sheaths. Kinking of the sheath and poor torque transfer throughout the length of the sheath cause difficulties in routing the sheath through the vasculature.

Hence, those skilled in the art have recognized a need for providing a peel-away sheath that is not susceptible to kinking and that efficiently transfers torsional loads throughout the sheath. The present invention fulfils these needs and others.

SUMMARY OF THE INVENTION

Briefly, and in general terms, the invention is directed to delivery systems for interventional devices and, more particularly, to a peel-away sheath that is not susceptible to kinking and which efficiently transfers torsional loads throughout the sheath.

In one aspect, the invention relates to a catheter sheath having an elongate tube having a proximal end, a distal end and a lumen therebetween. The elongate tube also includes at least one weakened area in a non-longitudinal pattern along the length of the tube. In a detailed aspect, the at least one weakened area includes two weakened areas positioned substantially diametrically opposite each other. In another detailed aspect, the at least one weakened area includes a slit extending partially into a wall of the catheter sheath. The at least one weakened area can include a slit extending partially into a wall of the catheter sheath, a groove within a wall of the catheter sheath or a series of perforations. The perforations include indentations which extend partially into a wall of the catheter sheath. In a further detailed aspect, the catheter sheath also includes a tab which is coupled to the proximal end of the catheter sheath. The tab has at least one weakened area. The number of weakened areas on the tab is equal to the number of weakened areas on the sheath and the weakened areas on the tab are aligned with the weakened areas on the sheath. The tab includes an annular shape having an outer diameter which is larger than the outer diameter of the sheath and an inner diameter which is substantially the same diameter as the diameter of the lumen in the sheath. The at least one weakened area of the tab can include a notch, a groove or a slit. The catheter sheath may also include fins which project radially from the catheter sheath and run longitudinally along the catheter sheath. The fins may be positioned at a proximal portion of the catheter sheath and about 90° apart circumferentially from the at least one weakened area in the tab.

In a second aspect, the invention relates to a catheter having a first sheath and a second sheath. The first sheath and second sheath each include a proximal end, a distal end, a lumen and at least one weakened area along its length. Further, the first sheath is positioned within the lumen of the second sheath.

In a detailed aspect, the at least one weakened area along each of the first and second sheaths includes a non-longitudinal pattern. The non-longitudinal pattern of the at least one weakened area along the first sheath and the second sheath includes a helical pattern. The helical pattern of the first sheath runs counter the helical pattern of the second sheath. In another aspect, the at least one weakened area along either the first sheath or the second sheath may include a non-longitudinal pattern. In a further aspect, the at least one weakened area along the length of each of the first sheath and the second sheath includes two longitudinal weakened areas which are circumferentially offset from each other, and the weakened areas of the first sheath are circumferentially offset from the weakened areas of the second sheath. In an additional aspect, the weakened areas of the first sheath are circumferentially offset approximately 90° from at least one of the weakened areas of the second sheath. Additionally, at least one of the first and second sheaths further includes at least one electrode and the weakened area extends through the at least one electrode.

In a third aspect, the invention relates to a catheter sheath having an elongate tube. The tube includes a proximal end, a distal end and a lumen therebetween. The catheter sheath also includes at least one pull wire. The at least one pull wire is integrally located within the wall of the sheath and extends throughout the length of the sheath in a non-longitudinal pattern. A proximal portion of the at least one pull wire extends from the proximal end of the sheath.

In a detailed aspect, the non-longitudinal pattern for the at least one pull wire is a helical pattern. In another aspect, the at least one pull wire includes two pull wires configured in a helical pattern about the sheath. However, in another aspect the two pull wires extend longitudinally throughout the sheath.

In a fourth aspect, the invention relates to a catheter sheath having an elongate tube. The tube includes a proximal end, a distal end and a lumen therebetween. The catheter sheath also includes at least one integral lumen which is located within the wall of the sheath. The at least one integral lumen extends throughout the length of the sheath.

In a detailed aspect, the at least one integral lumen may be configured in a non-longitudinal pattern about the sheath. The non-longitudinal pattern may be a helical pattern. In another aspect, the at least one integral lumen includes two integral lumens configured in a helical pattern about the sheath. However, in another aspect the at least one integral lumen extends longitudinally throughout the sheath and may include two integral lumens configured in a longitudinal pattern throughout the length of the sheath. In a further aspect, the catheter sheath also includes a filling material which is positioned throughout the length of the at least one integral lumen. Additionally, the filling material includes a non-adherent material.

In a fifth aspect, the invention relates to a reinforcing guide for a guide catheter. The reinforcing guide includes a longitudinal tube having a proximal end, a distal end and a lumen therebetween. The lumen has a diameter which is smaller than a diameter of the guide catheter. The reinforcing guide also includes a conical shape at the distal end of the exterior surface of the reinforcing guide. The reinforcing guide further includes a gap along its length having a width which is less than the diameter of the guide catheter. The tube is configured such that the width of the gap maybe temporarily expanded to a size greater than the diameter of the guide catheter.

In a detailed aspect, an angle of the gap opening is less than forty-five degrees. The gap may extend longitudinally throughout the length of the reinforcing guide. In another aspect, the gap may extend in a non-longitudinal pattern, such as a helical pattern. Further, a distal portion of the reinforcing guide may include a preformed curve.

In a sixth aspect, the invention relates to a reinforcing guide for a guide catheter. The reinforcing guide includes a longitudinal spiral band having a proximal end, a distal end and a lumen therebetween. The lumen has a diameter which is smaller than a diameter of the guide catheter. The reinforcing guide also includes a conical shape at the distal end of the exterior surface of the reinforcing guide. In a detailed aspect of the invention, the reinforcing guide includes a preformed curve.

In a seventh aspect, the invention relates to a guide catheter. The guide catheter includes a guide sheath having a first diameter, and a reinforcing guide which houses the guide sheath. The reinforcing guide includes a tube defining a lumen having a second diameter which is smaller than the first diameter. The tube has a gap along its length. The gap includes a width which is less than the first diameter. The tube is configured such that the width of the gap may be temporarily expanded to a size greater than the first diameter. The guide catheter also includes an insertion device which is adapted to facilitate installation of the reinforcing guide onto the guide sheath. The insertion device is coupled to an external surface of a proximal portion of the guide sheath.

In an eighth aspect, the invention relates to a guide catheter having a guide sheath. The guide sheath includes a first diameter. The guide catheter also includes a tube which houses the guide sheath. The tube defines a lumen having a second diameter which is smaller than the first diameter. The tube also has a gap along its length. The gap opening has a width which is smaller than the first diameter. The tube is configured such that the width of the gap may be temporarily expanded to a size greater than the first diameter. The guide catheter also includes a locking device which is adapted to maintain the tube in position relative to the guide sheath.

In one detailed aspect, the locking device includes a key device which is positioned at a proximal portion of the guide sheath and sized to fit within the gap of the tube. In another detailed aspect, the locking device includes a hub which is coupled to the proximal end of the tube and having a diameter which is larger than the tube. The locking device also includes a nut device having a first lumen having a first diameter, and a second lumen having a second diameter which is larger than the first diameter. The nut device also houses the hub of the locking device. The nut device also includes an internal threaded portion at a proximal portion of the second lumen. The locking device further includes a screw device having a lumen and an external threaded portion which is configured to mate with the internal threaded portion of the nut device. Additionally, the locking device includes a seal having a lumen.

In a further detailed aspect, the nut device is positioned on the tube with the hub positioned within the second lumen. The seal is positioned on the tube, proximal to the hub of the tube. The screw device is positioned on the guide sheath, proximal to the seal with the threaded portion of the screw device positioned at a distal portion of the screw device. Also, the nut device and the screw device are screwed together, thereby causing the nut device to push the hub into a distal end of the seal and the screw device to push into a proximal end of the seal. This causes the lumen of the seal to become smaller and to form a friction grip with the guide sheath.

These and other aspects and advantages of the invention will become apparent from the following detailed description and the accompanying drawings which illustrate by way of example the features of the invention.

BRIEF DESCRIPTION OF THE DRAWINGS

FIG. 1a is a perspective view of a peel-away sheath;

FIG. 1b is a cross-section view of the construction of the peel-away sheath taken along the line 1b—1b from FIG. 1a;

FIG. 5a is a plan view of a sheath having two pull wires within a wall of the sheath;

FIG. 5b is a cross-section view of the construction of the sheath having two pull wires of FIG. 5a taken along the line 5b—5b;

FIG. 5c is a perspective view of the sheath having two pull wires of FIG. 5a depicting the wires being pulled through a wall of the sheath and the sheath being separated;

FIG. 6a is a plan view of a sheath having two integrated lumens within a wall of the sheath and an alternative filler material within one of the integrated lumens;

FIG. 6b is a cross-section view of the construction of the sheath having two integrated lumens within the wall of the sheath of FIG. 6a taken along the line 6b—6b;

FIG. 6c is a perspective view of the sheath having two integrated lumens within the wall of the sheath of FIG. 6a depicting the sheath being separated;

FIG. 7a is a perspective view of a peel-away sheath with a reinforcing guide external the sheath;

FIG. 7b is a cross-section view of the sheath with the reinforcing guide external the sheath of FIG. 7a taken along the line 7b—7b;

FIG. 7c is a plan view of peel-away sheath with a reinforcing guide external the sheath;

FIG. 10a is a perspective view of a guide sheath having an insertion device for facilitating the installation of a reinforcing guide onto the guide sheath.

FIG. 10b is a perspective view of the guide sheath having the insertion device of FIG. 10a and including the reinforcing guide being installed onto the guide sheath through the use of the insertion tool.

DETAILED DESCRIPTION OF THE PREFERRED EMBODIMENTS

Figure 1:
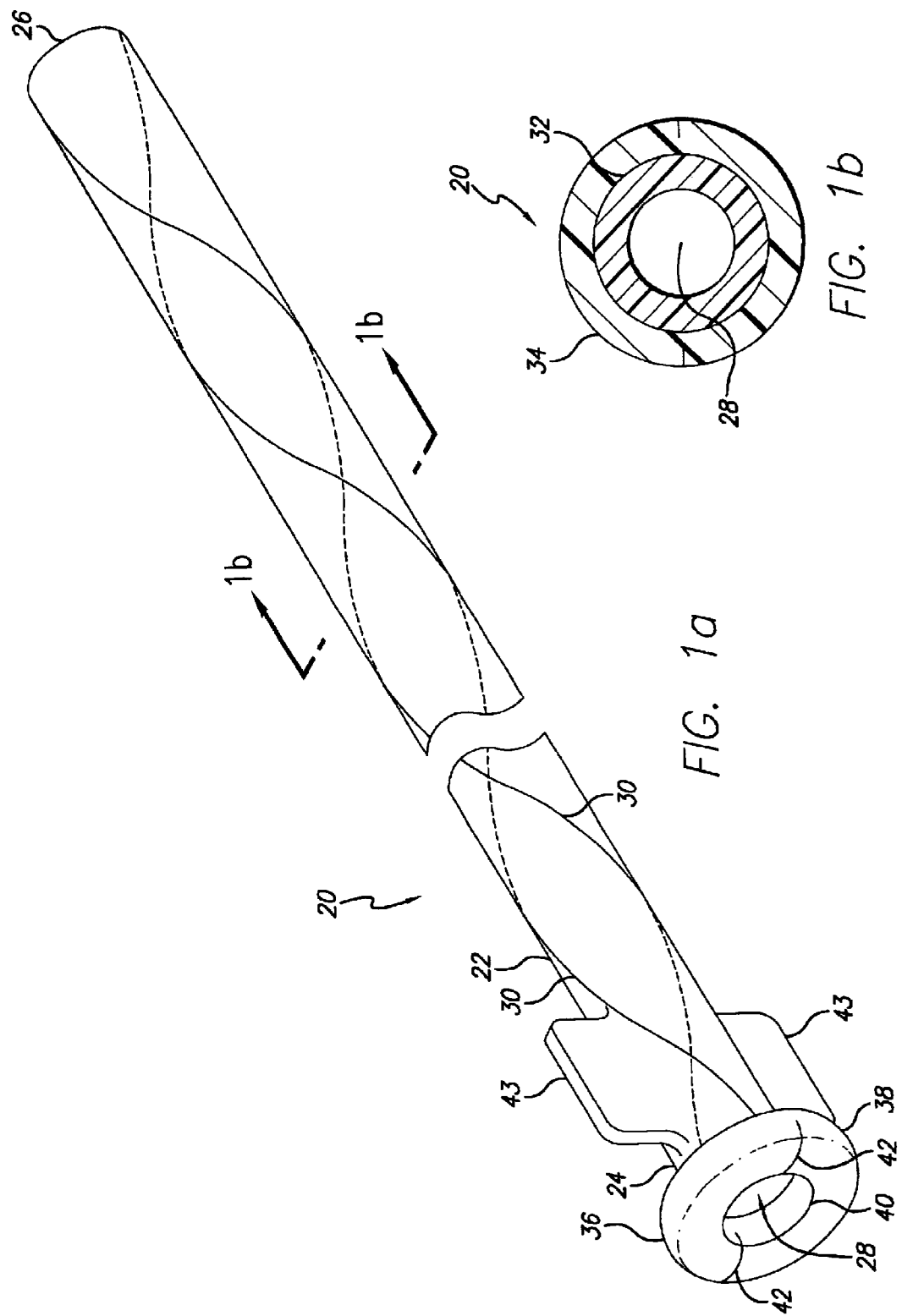

Referring now to the drawings, wherein the reference numerals denote like or corresponding parts throughout the figures, and particularly to FIG. 1a, there is shown a longitudinal catheter sheath 20 including an elongate tube 22 having a proximal end 24, a distal end 26 and a lumen 28 throughout its length. The sheath 20 also includes at least one weakened area 30 which extends along the length of the sheath in a non-longitudinal pattern which facilitates peeling of the sheath. (FIG. 1a depicts two weakened areas arranged in a helical pattern.)

With reference to FIG. 1b, which is a cross-sectional view taken from FIG. 1a, the sheath 20 may include a layered composite. As depicted in this embodiment, the inner layer 32 may be a hollow tube made of a polymer possessing a high modulus of elasticity, such as polyetheretherketone (PEEK). The outer layer 34 may be made of a flexible, intermediate-durometer polymer such as polyether block amide, known commercially as Pebax™. In one embodiment, the outer layer 34 includes a 63D (shore "D" hardness value) hardness scale Pebax™ tube. The two layers 32, 34 may be bonded together by the simultaneous application of heat and pressure. The inner 32 layer and outer 34 layer may be formed by processes such as extruding.

Referring again to FIG. 1a, a breakable tab 36 is coupled to the proximal end 24 of the sheath 20. The tab 36 serves as an interface between the sheath 20 and a handle (not shown). The tab 36 includes an annular shape and has a larger outer diameter 38 than the sheath 20 while the inner diameter 40 is substantially the same as the lumen 28 diameter of the sheath. The tab 36 is formed of a material which is harder than the sheath 20, such as polycarbonate or ABS. The tab 36 includes at least one weakened area 42 defined by a notch, a groove or a slit which facilitates the breaking of the tab so that the sheath 20 can be pulled apart along the at least one weakened area 30 of the sheath. The number of reduced areas 42 in the tab 36 preferably is equal to the number of weakened areas 30 in the sheath 20, hence two notches are depicted in FIG. 1a. The tab 36 is coupled to the sheath 20, such as by an adhesive bond, heat and pressure, or a mechanical joint, in such manner that each of the reduced areas 42 of the tab is substantially aligned with each of the weakened areas 30 in the sheath.

To further facilitate the breaking of the tab 36, a proximal portion of the sheath 20 may include fins 43 which are positioned about 90° apart circumferentially from the weakened areas 42 in the tab. The fins 43 may project radially from the sheath 20 and may run in a longitudinal direction along the sheath. The tab 36 may be broken by pulling the fins 43 in substantially opposite directions. The fins may be formed of Pebax, polycarbonate, ABS, or other suitable material. The fins 43 may be coupled to the sheath 20 through an adhesive bond, a mechanical joint, or other satisfactory manner.

Referring again to FIG. 1a, the two weakened areas 30 within the sheath 20 may include such forms as slits, grooves, perforations or other suitable configurations. The slits are defined as narrow openings which are added to the sheath, such as by scoring with a blade. The grooves are defined as wider openings than the slits which may be incorporated into the sheath by an extrusion die or other sheath fabrication tool. When perforations are utilized to create the weakened areas, it is preferable that the perforations are a series of indentations which do not extend completely through the wall of the sheath so that air does not flow through them. The weakened areas 30 may begin their non-longitudinal pattern at the proximal end 24 of the sheath 20, immediately distal to the breakable tab 36. Alternatively, the weakened areas 30 may begin at the proximal end 24 of the sheath 20 in a longitudinal pattern which extends along the length of the sheath for a relatively short distance, in order to facilitate initial sheath peeling, and then transition into the non-longitudinal pattern. To further facilitate peeling of the sheath, in one embodiment the two weakened areas 30 may be positioned diametrically opposite each other throughout the length of the sheath 20. Although the invention is described as having two weakened areas, the invention is not limited to two weakened areas. The sheath may alternatively include only one weakened area or more than two weakened areas.

A benefit of non-longitudinal weakened areas, as opposed to the longitudinal weakened areas found in prior art sheathes, is that the non-longitudinal weakened areas distribute stress more efficiently along the thinner, weaker wall of the sheath along the weakened areas. This improved stress distribution improves strength characteristics and kink resistance of the sheath. Further, the non-longitudinal pattern of the weakened area permits greater torsional strength for manipulation and rotation of the sheath in comparison to sheaths having longitudinal weakened areas.

The weakened areas 30 may be added to the sheath 20 either during or after the fabrication of the sheath. For example, in extruded sheaths, the weakened areas maybe added as part of the extrusion process by passing the extruding sheath through a tooling device (not shown), such as a tooling jig, which is configured to add desired weakened areas, such as slits, grooves or perforations to the sheath. Alternatively, the extruded sheath can be fully extruded and cured, and then passed through the tooling device for adding the desired weakened areas. To create a helical weakened area, either the sheath, the tooling device or both may be rotated relative each other while the sheath passes through the tooling device. Controlling the pitch of the helical pattern of the weakened areas is a function of the rate at which the sheath passes through the tooling device and the rotation speed between the sheath and the tooling device. The pitch of the helical pattern maybe balanced to facilitate easy peeling of the sheath coupled with increased strength of the sheath.

Figure 2:
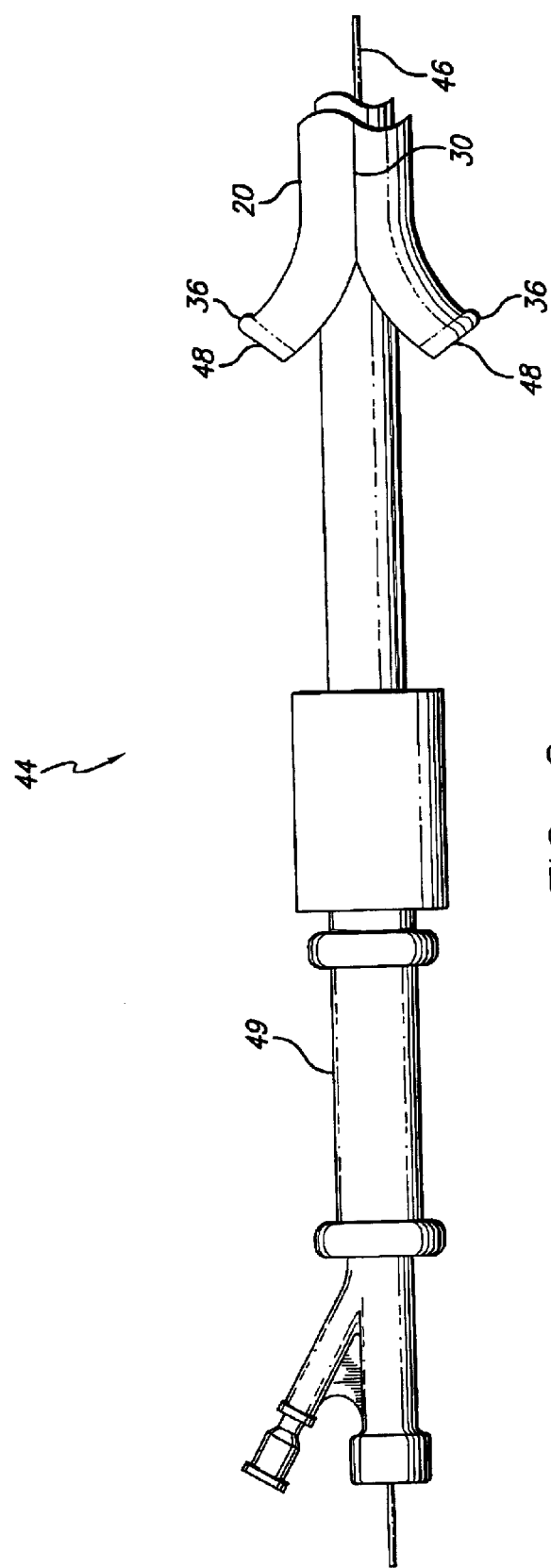
FIG. 2 is a plan view of a catheter utilizing the peel-away sheath of FIG. 1a with the sheath being peeled away.

Referring to FIG. 2, the sheath 20 having at least one non-longitudinal weakened area 30 forms part of a guiding catheter 44 which may be used to deliver an interventional device (not shown) to a biological site (not shown) within a patient. The interventional device may be coupled to the distal end of a guide wire 46 which is positioned within the sheath 20. After the interventional device is delivered to the biological site, it is often desirable to remove the sheath 20 of the guiding catheter from the patient while leaving the guide wire 46 within the patient and the interventional device at the biological site. To remove the sheath 20 of the present invention from the patient, the tab 36 is broken along the reduced areas (not shown in FIG. 2), thereby forming separate tabs 48. The separate tabs 48 are pulled apart from each other, thereby causing the sheath 20 to split along the weakened areas 30 and permitting the split portions of the sheath to be peeled from the guide wire 46. The portion of the sheath 20 external to the patient is split and the sheath retracted toward a catheter handle 49, thereby exposing more of the non-split portion of the sheath. This step maybe repeated until the entire sheath 20 is removed from the patient and peeled from the guide wire 46.

Figure 3:
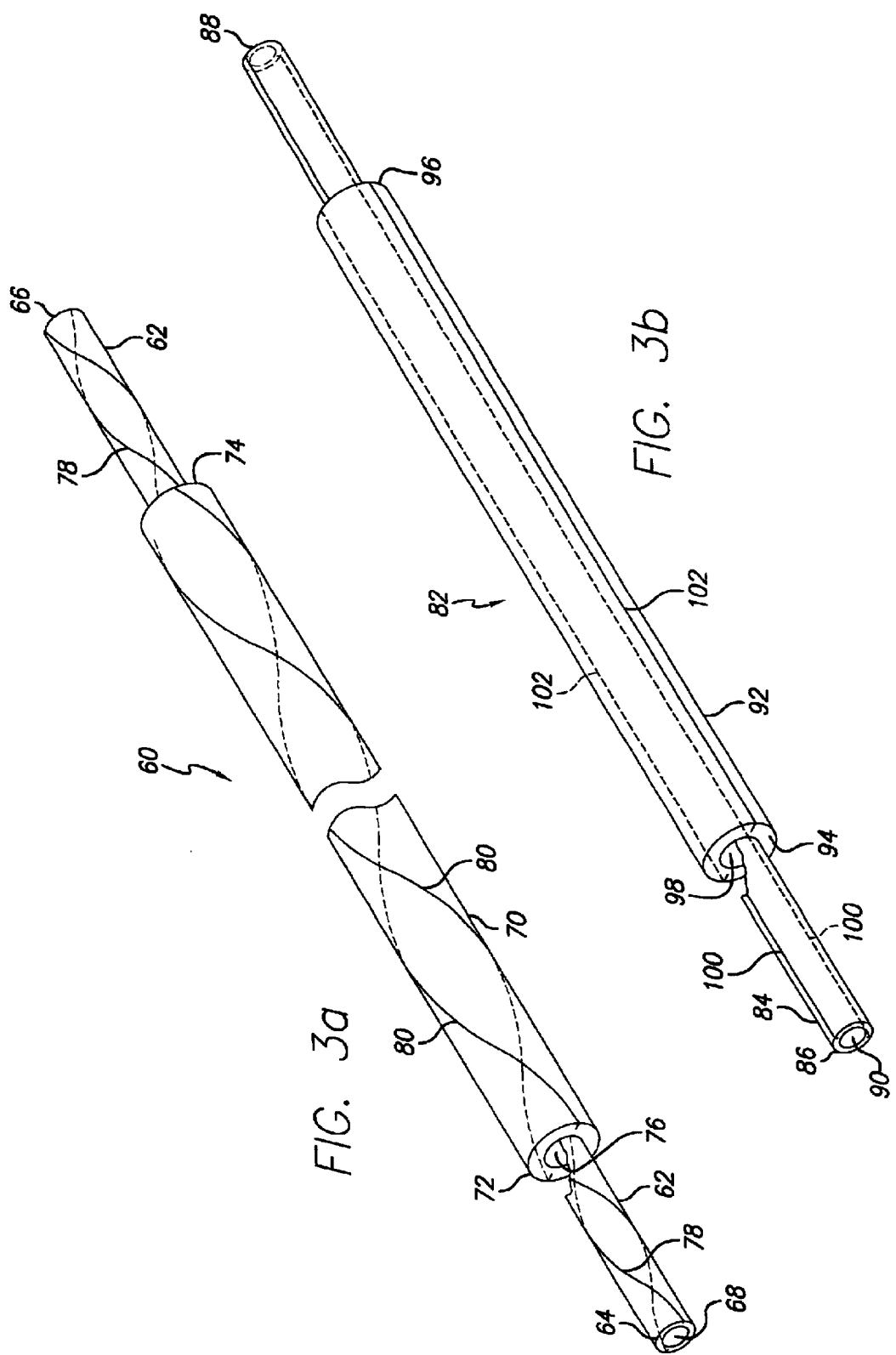
FIG. 3a is a perspective view of a dual-sheath assembly having two peel-away sheaths.
FIG. 3b is a perspective view of an alternative embodiment of the dual-sheath assembly.

Referring now to FIG. 3a, a dual sheath 60 embodiment is depicted. The dual sheath 60 embodiment includes a first sheath 62 (inner sheath) having a proximal end 64, a distal end 66 and a lumen 68 therebetween, and a second sheath 70 (outer sheath) having a proximal end 72, a distal end 74 and a lumen 76 therebetween with the first sheath positioned within the lumen of the second sheath. Such dual sheath embodiments 60 may be used for medical procedures, such as guiding pacing or defibrillation leads into the coronary sinus of a patient's heart or into other biological areas. In one embodiment, each of the first 62 and second 70 sheaths includes at least one weakened area 78, 80 having a non-longitudinal pattern, such as a helical pattern, similar to those within the sheath of FIG. 1a. (FIG. 3a depicts both the inner sheath and the outer sheath having two weakened areas arranged in a helical pattern.) In this embodiment, the non-longitudinal pattern of the inner sheath 62 may run counter to the non-longitudinal pattern of the outer sheath 70 so that each sheath supports the other during axial rotation of the sheaths. However, if desired, the non-longitudinal pattern of the inner sheath 62 may alternatively run the same direction as the non-longitudinal pattern of the outer sheath 70. Further, the inner 62 and outer 70 sheaths may be either of equal length or differing lengths, depending on the proposed use of the sheaths.

In another embodiment, either the inner 62 or outer 70 sheath may include a preformed, curved profile (not shown) which may be used to induce a curve within the other sheath. Alternatively, both the inner and outer sheaths may include a preformed, curved profile (not shown) which may induce a curve in the other sheath. Such preformed sheaths may be used to facilitate directing the sheaths to a particular anatomical position in a patient, such as within the coronary sinus. In a further embodiment, the outer sheath 70 may include weakened areas while the inner sheath 62 may have no weakened areas so that the inner sheath supports the outer sheath during use.

Referring to FIG. 3b, another dual sheath 82 embodiment includes a first sheath 84 (inner sheath) having a proximal end 86, a distal end 88 and a lumen 90 therebetween, and a second sheath 92 (outer sheath) having a proximal end 94, a distal end 96 and a lumen 98 therebetween. The inner sheath 84 is positioned within the lumen 98 of the outer sheath 92. However, rather than each sheath 84, 92 having non-longitudinal weakened areas, as with the dual sheath 60 embodiment of FIG. 3a, each of the sheaths includes two longitudinal weakened areas 100, 102 which extend the length of the sheaths, similar to the longitudinal weakened areas in prior art sheaths. The longitudinal weakened areas 100 on the inner sheath 84 are diametrically opposed to each other along the length of the sheath. The longitudinal weakened areas 102 on the outer sheath 92 are also diametrically opposed to each other. However, in order that the inner sheath 84 and the outer sheath 92 support each other, the sheaths are positioned such that the weakened areas 100 of the inner sheath are about 90° apart circumferentially from the weakened areas 102 of the outer sheath. Positioning the weakened areas 100, 102 of the inner 84 and outer 92 sheaths about 90° apart from each other also improves the kink resistance of the dual sheath 82 embodiment in comparison to a single sheath having longitudinal weakened areas.

Figure 4:
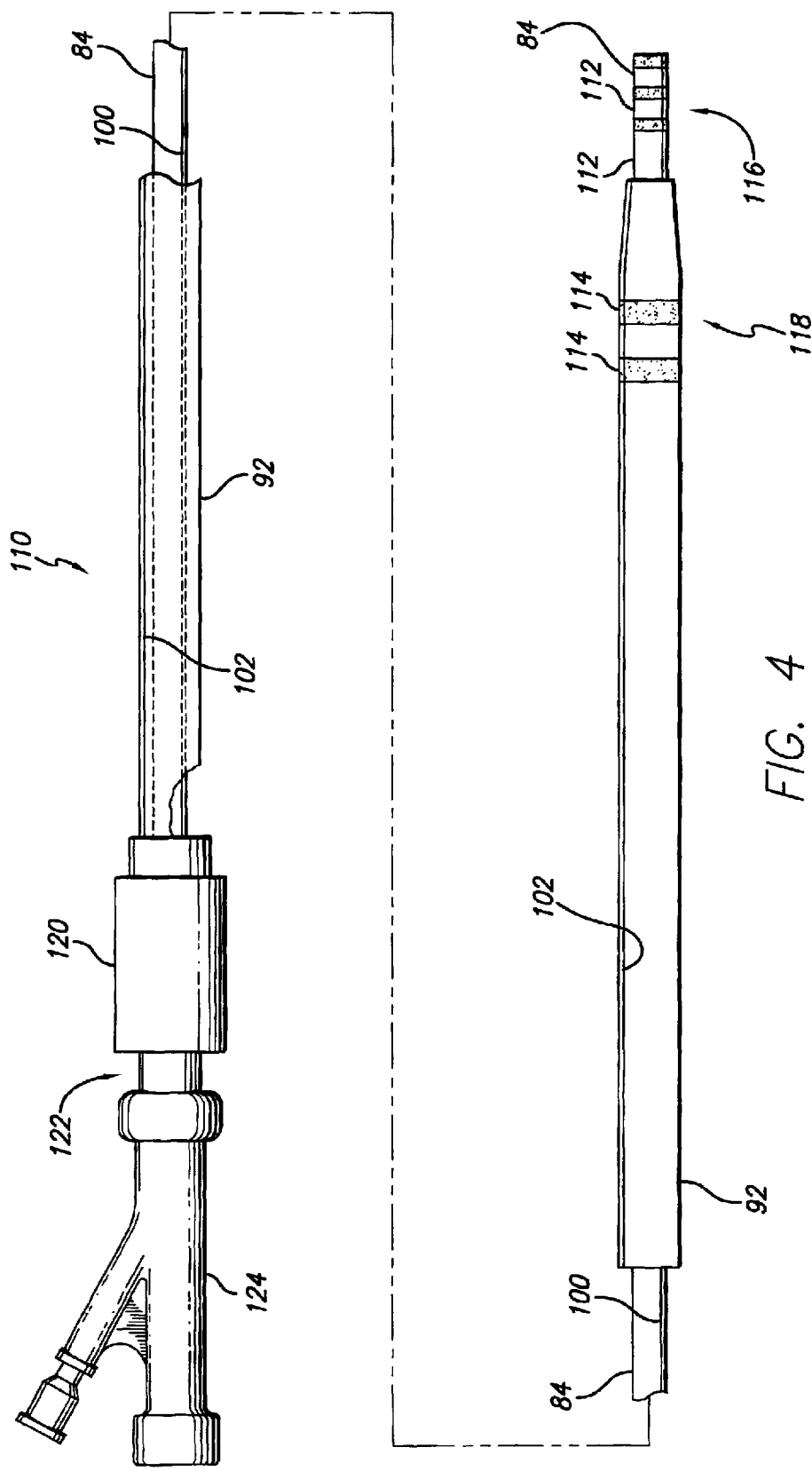
FIG. 4 is a plan view of a catheter employing the dual-sheath assembly of FIG. 3b.

Referring to FIG. 4, a catheter 110 which utilizes the dual sheath 82 embodiment of FIG. 3b is depicted. In this embodiment, at least one band electrode 112, 114 maybe disposed within a distal portion 116, 118 of both the inner sheath 84 and the outer sheath 92. To facilitate peeling of the entire length of the inner 84 and outer 92 sheaths, the weakened areas 100, 102 within the sheaths extend through the band electrodes 112, 114 such that the band electrodes split during the peeling operation. Lead wires (not shown) for the band electrodes 112, 114 traverse the lumens 90, 98 of the sheaths 84, 92 with distal ends of the lead wires being coupled to the band electrodes. Proximal ends of the lead wires exit through the proximal ends 86, 94 of the sheaths and are coupled to a lead connector 120 which is coupled to a distal portion 122 of a handle 124, such as a rotatable hemostatic valve.

In one embodiment, devices such as the lead connector 120 may be permanently coupled to the handle 124. Being significantly larger than the catheter sheaths 84, 92, the lead connector 120 prevents the sheaths from merely slipping over the lead connector for removal from the catheter 110. Therefore, the sheaths 84, 92 include the weakened areas 100, 102 to permit the sheaths to be peeled from the catheter 110 during removal of the sheaths while avoiding interference with permanently installed devices within the catheter. Further, in order to peel and remove the entire length of the sheaths 84, 92 from the catheter 110, the weakened areas 100, 102 must extend throughout the length of the sheaths.

With reference to FIGS. 5a and 5b, another embodiment of the present invention includes a longitudinal catheter sheath 130 having a proximal end 132, a distal end 134 and a lumen 136 throughout its length. At least one pull wire 138 (two pull wires are depicted in FIGS. 5a and 5b) is integrally located within the wall 140 of the sheath. The at least one pull wire 138 may be introduced into the wall 140 of the sheath 130 during fabrication of the sheath using techniques that are well known in the art, such as an extrusion process. The at least one pull wire 138 extends throughout the length of the sheath 130 with a proximal portion 142 of the pull wire extending from the proximal end 132 of the sheath to a location proximal the proximal end of the sheath. In one embodiment, the pull wire 138 is configured in a helical pattern about the sheath 130 while in another embodiment the pull wire extends longitudinally throughout the sheath. (FIG. 5a depicts the two pull wires extending longitudinally throughout the sheath.)

Having the at least one pull wire 138 positioned within the wall 140 of the sheath 130 results in the area of the sheath wall around the at least one pull wire having a smaller cross section. Referring to FIG. 5c, to remove the sheath 130 from catheter during use, the proximal portion 142 of the pull wire 138 which extends from the proximal end 132 of the sheath is pulled in a direction away from a longitudinal axis 144 of the sheath. Due to the smaller cross section of the sheath 130 in the area of the at least one pull wire 138, the at least one pull wire may easily tear through the wall 140 of the sheath, resulting in a weakened sheath wall with a further reduced cross section. The remaining reduced cross section is then easily torn and the sheath 130 removed from the catheter. Since the removal of the at least one pull wire 138 sufficiently reduces and weakens the wall 140 of the sheath 130 for peeling and removing, the sheath may be constructed from higher durometer materials, thereby improving torsion strength and kink resistance of the sheath.

In FIGS. 5a and 5b, two pull wires 138 are depicted substantially diametrically opposite each other throughout the length of the sheath 130. Having at least two pull wires 138 increases the ease with which the sheath 130 may be peeled from the catheter over sheaths having only one pull wire. With the pull wires 138 positioned substantially diametrically opposite each other, when the pull wires are pulled away to tear the sheath 130 and the reduced cross section is torn apart, a resulting opening in the sheath provides practically no interference with the catheter during removal of the sheath from the catheter.

Referring to FIGS. 6a and 6b, another embodiment of the invention includes a catheter sheath 150 having a proximal end 152, a distal end 154 and a lumen 156 throughout its length. The sheath 150 also includes at least one integral lumen 158 (two integral lumens are depicted in FIGS. 6a and 6b) within a wall 160 of the sheath. The at least one integral lumen 158 may be produced within the wall 160 of the sheath 150 during fabrication of the sheath using techniques that are well known in the art, such as an extrusion process. The at least one integral lumen 158 extends throughout the length of the sheath 150 in a pattern, such as a helical or longitudinal pattern. Similar to the sheath 130 of FIGS. 5a and 5b, having at least two integral lumens 158 positioned diametrically opposite each other provides practically no interference between the sheath 150 and the catheter during removal of the sheath from the catheter.

The at least one integral lumen 158 within the wall 160 of the sheath 150 results in an area of the sheath wall having a reduced cross section 162 and relative weakness in comparison to the remainder of the sheath. The reduced cross section 162 is attained without the use of a slit, groove or series of perforations along the length of the sheath. Referring to FIG. 6c, to remove the sheath 150 from a catheter, the operator tears the sheath along the at least one integral lumen 158 and peels the sheath from the catheter.

To increase the strength of the sheath 150 having the at least one integral lumen 158 within the wall 160 of the sheath, the at least one integral lumen may be filled with a filling material 164, such as a wire or cord. (Only one of the lumens 158 depicts the filling material 164.) If the filling material 164 is adhered or bonded to the surface of the at least one integral lumen 158, tearing and peeling of the sheath becomes difficult because the filling material essentially is part of the wall of the sheath. Therefore, the filling material 164 in the present embodiment includes a material which does not adhere to the surface of the at least one integral lumen 158. Such materials may include Fluorinated Ethylene Propylene (FEP), polytetrafluoroethylene (PTFE, known commercially as Teflon™), expanded polytetrafluoroethylene (ePTFE), Polyimide, or other suitable materials.

The filler material 164 may be introduced into the at least one integral lumen 158 through methods that are well known in the art. For example, the filler material 164 can be added to the at least one integral lumen 158 during fabrication of the sheath 150, such as by an extrusion process. Alternatively, the filler material 164 may be added to the at least one integral lumen 158 after the fabrication of the sheath 150. For example, the filler material 164 can be pulled through the at least one integral lumen 158. To fully encapsulate the filler material 164, the sheath 150 may then be heat processed to remove the space between the surface of the at least one integral lumen 158 and the filler material.

To further increase the torsion strength and kink resistance of the sheath 150 with the at least one integral lumen 158, the sheath may include a layer of a braided material (not shown), such as a polymeric material, which is susceptible to tearing. Such a layer of braided material increases the strength of the sheath while maintaining the ability to be torn and peeled.

Many current guide catheters which are utilized to direct guide sheaths to specific biological sites within a patient are limited in their application due to fixed shapes of the guide sheaths. With reference to FIGS. 7a and 7b, a reinforcing guide 170 may be employed in connection with a guide catheter 172. The reinforcing guide 170 maybe placed over the guide sheath 174 portion of the guide catheter 172 to increase rigidity or support of the guide sheath after the guide sheath is placed at the biological site, such as the coronary sinus, without removing the guide sheath from the biological site. The reinforcing guide 170 may also be used to change the shape of catheters which include a preformed shape, such as a curve.

The reinforcing guide 170 includes a longitudinal tube 176 having a proximal end 178, a distal end 180 and a lumen 182 therebetween. An exterior surface 184 of a distal end portion 186 of the reinforcing guide 170 includes a conical shape 188 to reduce the risk of the distal end of the reinforcing guide injuring a wall of the biological lumen and to facilitate travel of the reinforcing guide through the biological lumen of a patient. In one embodiment, the reinforcing guide 170 may be formed of an extrudable polymer, such as PEEK, FEP, polyethylene, Pebax, or other suitable material.

The reinforcing guide 170 includes a split 190 throughout its length, thereby forming a gap 192 along the length of the reinforcing guide. The gap 192 may be either longitudinal or in a non-longitudinal pattern, such as a helical pattern. In one embodiment, the angle 194 of the gap 192 opening is less than forty-five degrees. Gaps 192 of larger sizes may be included, however, larger gaps increase the likelihood that the reinforcing guide 170 may inadvertently separate from the guide sheath 174. To help ensure that the reinforcing guide 170 remains in place on the guide sheath 174, the diameter of the lumen 182 of the reinforcing guide is smaller than the diameter of the exterior 196 of the guide sheath. This places the circumference of the reinforcing guide 170 in tension and enables the reinforcing guide to exert positive pressure against the exterior surface 196 of the guide sheath 174, thereby helping the reinforcing guide to remain in place.

Referring to FIG. 7c, an alternative embodiment of a reinforcing guide 214 includes a longitudinal spiral band 216 having a proximal end 218, a distal end 220 and a lumen 222 therebetween. An exterior surface 224 of a distal end portion 226 of the reinforcing guide 214 may include a taper 228. The taper 228 may be formed by reducing the thickness of the spiral band 216 material in the tapered area. In one embodiment, the reinforcing guide 214 maybe formed of PEEK, FEP, polyethylene, Pebax, or other suitable polymers. Alternatively, the reinforcing guide 214 may be formed of metals, such as stainless steel, titanium, or other biocompatible alloys.

To help ensure that the reinforcing guide 214 remains in place on the guide sheath 174, the diameter of the lumen 222 of the reinforcing guide is smaller than the diameter of the exterior of the guide sheath, thereby placing the circumference of the reinforcing guide in tension and enabling the reinforcing guide to exert positive pressure against exterior surface of the guide sheath. The reinforcing guide 214 having the spiral band 216 maybe sufficiently flexible to conform to the profile of the guide sheath 174, yet provide support to the guide sheath.

Figure 7D:
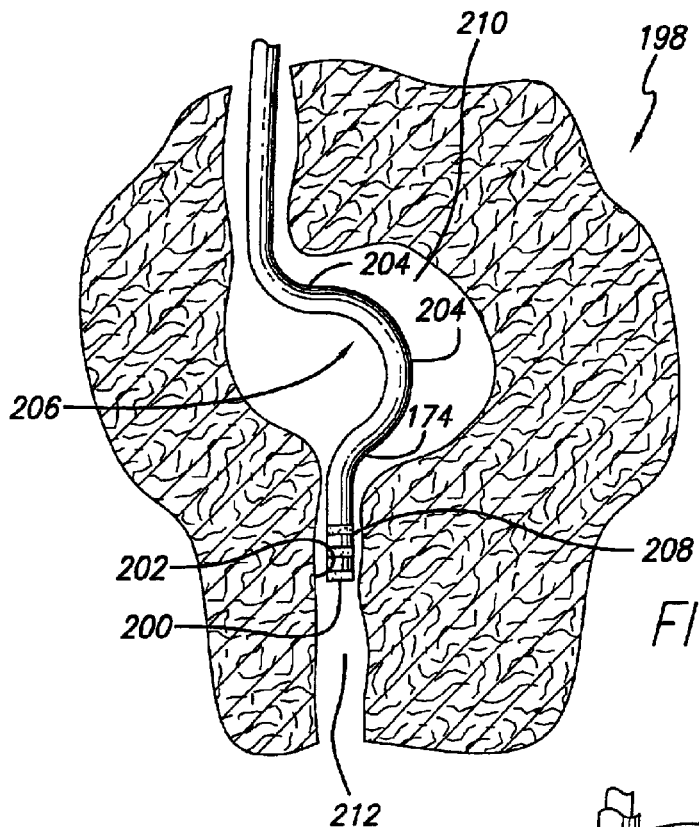
FIG. 7d is a plan view of the sheath of FIG. 7a within a biological body, the sheath having a preformed curve.
Figure 7E:
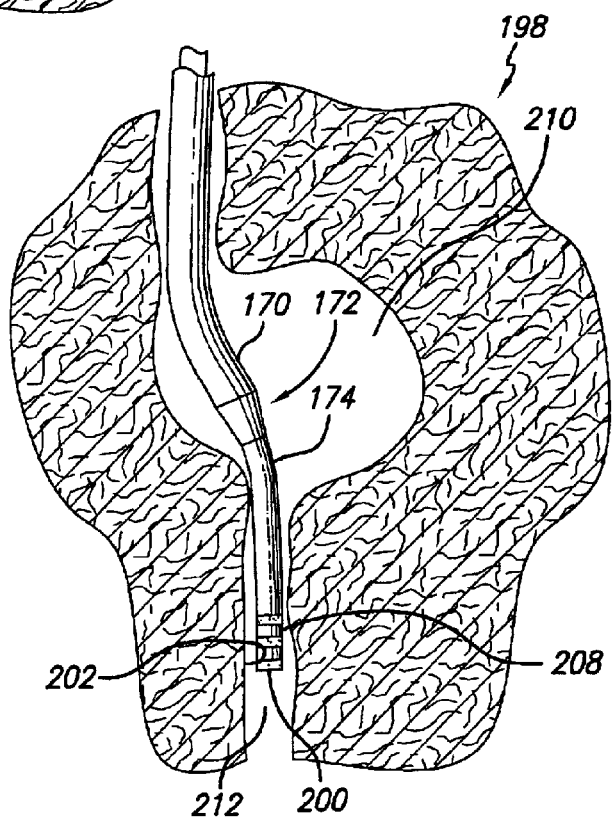
FIG. 7e is a plan view of the sheath and reinforcing guide of FIG. 7a within the biological body with the reinforcing guide altering the shape of the preformed curve of the sheath.

Referring to FIG. 7d, the guide sheath 174 may be inserted into a biological body 198 and a distal end 200 of the guide sheath delivered to a biological site 202. The gap 192 within the reinforcing guide 170 may then be spread open (not shown) to clear the diameter of the guide sheath 174 and then onto the guide sheath as shown in FIG. 7e. With the reinforcing guide 170 in place on the guide sheath 174, the reinforcing guide may be translated longitudinally along the length of the guide sheath to a desired position to effect the shape of, or provide support to, the guide sheath. In an alternative embodiment, the reinforcing guide 170 may be installed onto the guide sheath 174 prior to insertion of the guide sheath into the biological body 198. By adjusting the longitudinal placement of the reinforcing guide 170 relative to the guide sheath 174, bend points 204 in the guide sheath, or preformed shapes, can be changed or supported.

For example, FIG. 7d depicts a guide sheath 174 having a curved portion 206. The curved portion 206 of the guide sheath 174 is positioned within a biological cavity 210 and the distal end 200 of the guide sheath is positioned within a biological lumen 212, such as the coronary sinus. The distal end 180 of the reinforcing guide 170 is depicted proximally of the curved portion 206 of the guide sheath 174. As depicted in FIG. 7e, when the reinforcing guide 170 is translated distally to surround the curved portion 206 of the guide sheath 174, the curved portion of the guide sheath straightens, thus resulting in the distal end 200 of the guide sheath advancing distally and further into the biological lumen 212. A further result is that more force is applied to the distal-end portion 208 of the guide sheath 174 to help prevent the distal end 200 of the guide sheath from pulling out of the biological lumen 212 when other devices are advanced or removed from the guiding catheter 172.

In an alternative embodiment (not shown), the reinforcing guide 170 may include a preformed shape, such as a curve, which supports curves within the guide sheath 174. In a further embodiment, the preformed shape in the reinforcing guide 170 is equally curved or less curved than the guide sheath 174.

Figure 8A:
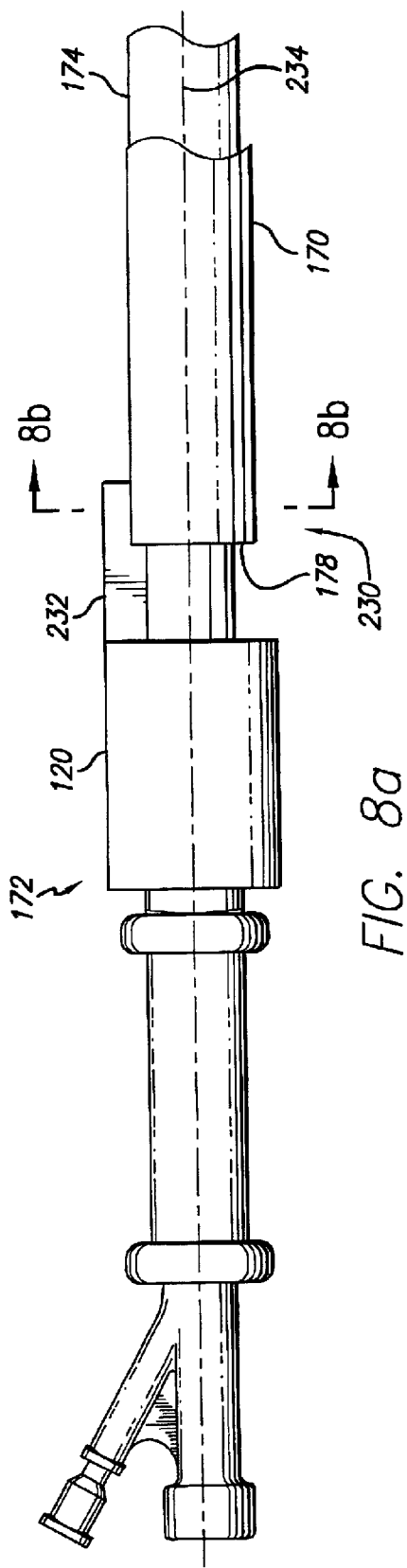
FIG. 8a is a plan view of a proximal portion of a catheter with the reinforcing guide of FIG. 7a and including a key device to prevent relative rotational movement between the sheath and the reinforcing guide.
Figure 8C:
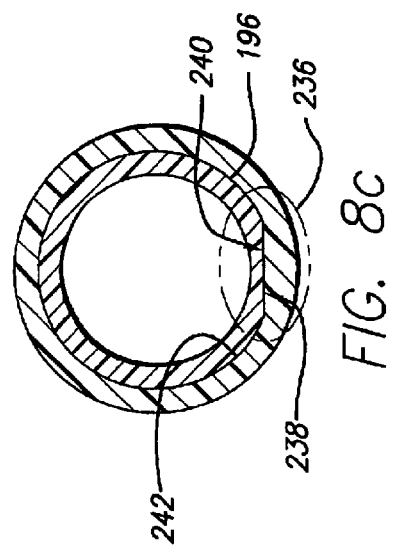
FIG. 8c is a cross-section of an alternative embodiment of the key device of FIG. 8b.
Figure 8B:
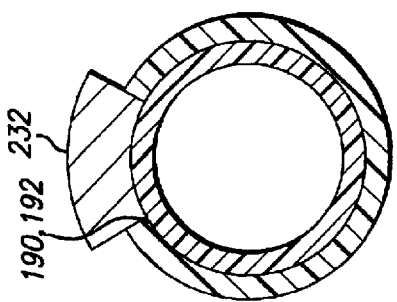
FIG. 8b is across-section view of the sheath and reinforcing guide of FIG. 8a depicting the interaction between the key device and the reinforcing guide taken along line 8b—8b.

In some situations, such as when the guide sheath includes a longitudinal weakened area or a preformed shape, it may be desirable to include a mechanism to prevent the reinforcing guide from rotating about the guide sheath. In other situations it may also be desirable to lock the longitudinal position of the reinforcing guide relative to the guide sheath. Referring to FIGS. 8a and 8b, a proximal portion 230 of the guide catheter 172 of FIG. 7c may include a key device 232 which fits within the gap 192 of the reinforcing guide 170. The key device 232 acts as a mechanical stop to prevent the reinforcing guide 170 from rotating about an axis 234 of the guide sheath 174, but permits the reinforcing guide to translate longitudinally along the length of the guide sheath. Referring to FIG. 8c, an alternative embodiment of a key device 236 includes non-circular mating surfaces 238,240, such as flats, on the exterior surface 196 of the guide sheath 174 and on the lumen surface 242 of the reinforcing guide 170.

Figure 9:
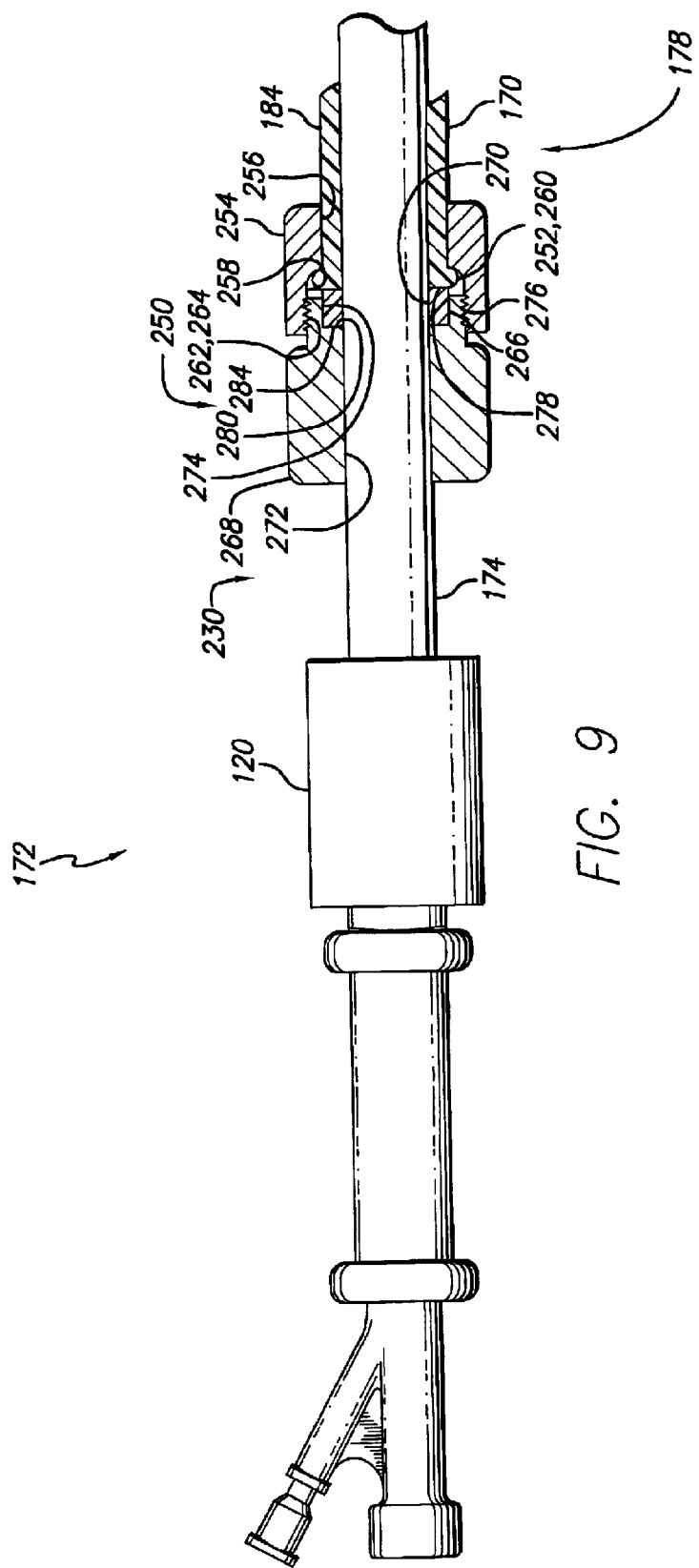
FIG. 9 is a plan view of a proximal portion of a catheter with the reinforcing guide of FIG. 7a and including a locking device to prevent relative rotational and longitudinal movement between the sheath and the reinforcing guide.

Referring to FIG. 9, a locking device 250 located at the proximal portion 230 of the guide catheter 172 may be utilized to maintain the reinforcing guide 170 at a desired position along the guide sheath 174. In one embodiment, the locking device 250 includes a hub 252 having a diameter larger than the reinforcing guide 170 at the proximal end 178 of the reinforcing guide. In one embodiment, the hub 252 includes a gap (not shown) which corresponds with the gap 192 (FIG. 7b) in the reinforcing guide 170. A nut device 254 portion of the locking device 250 includes a first lumen 256 having a first diameter and a second lumen 258 having a second diameter which is larger than the first diameter. The first lumen 256 is sized to fit over the exterior surface 184 of the reinforcing guide 170, but is smaller than the diameter 260 of the hub 252 on the reinforcing guide. The second diameter is larger than the diameter 260 of the hub 252 on the reinforcing guide 170, thus allowing the second lumen 258 to slide over and house the hub. A proximal portion 262 of the second lumen 258 includes an internal, or female, threaded portion 264.

The locking device 250 also includes a seal 266 and a screw device 268. The seal 266 includes a lumen 270 through which the guide sheath 174 can pass. The screw device 268 includes a first lumen 272 (proximal lumen) and a second lumen 274 (distal lumen) through which the guide sheath 174 can pass, the second lumen being larger than the first lumen. The screw device 268 also includes an external, or male, threaded portion 276 which is configured to mate with the internal threaded portion 264 of the nut device 254. In use, the seal 266 is installed onto the guide sheath 174 and is placed in contact with a proximal face 278 of the hub 252 on the reinforcing guide 170. The screw device 268 is also installed onto the guide sheath 174 then advanced toward the reinforcing guide 170 until a face 280 between the first 272 and the second 274 lumens of the screw device 268 contacts the seal 266. The nut device 254, however, is installed onto the reinforcing guide 170 and located so that the hub 252 of the reinforcing guide is positioned within the second lumen 258 of the nut device. The nut device 254 and the screw device 268 are then screwed together, thereby causing the nut device to push the hub 252 into a distal end 282 of the seal 266 and the screw device to push into a proximal end 284 of the seal. The opposing compressive forces on the seal 266 causes the seal lumen 270 to become smaller, resulting in a friction grip with the guide sheath 174. As a result, rotational and longitudinal movement between the guide sheath 174 and the reinforcing guide 170 is restricted.

Referring to FIGS. 10a and 10b, a further embodiment of the invention includes an insertion device 300 to facilitate installation of the reinforcing guide 170 onto the guide sheath 304. The insertion device 300 may be coupled to a proximal portion 306 of the guide sheath 304. The insertion device 300 may include a tubular portion 308 which is positioned around the proximal portion 306 of the guide sheath 304. A lobe portion 310 may project from the tubular portion 308 and extend throughout the length of the insertion device 300. The lobe portion 310 may include a curved surface 312 having an apex 314 and two side walls 316. The curved surface 312 may be sufficiently small to fit within the opening of the gap 192 of the reinforcing guide 170. The two side walls 316 may be either curved or substantially flat, and positioned between tangents on the curved surface 312 and the tubular portion 308. In an alternative embodiment (not shown), the insertion device 300 may include a longitudinal split to facilitate removal of the insertion device from the guide sheath 304.

To install the reinforcing guide 170 onto the guide sheath 304 through the use of the insertion device 300, the distal end 180 of the reinforcing guide is placed against the curved surface 312 of the insertion device such that the apex 314 of the curved surface is positioned within the gap 192 of the reinforcing guide. The reinforcing guide 170 may then be translated toward the tubular portion 308 of the insertion device 300 to permit the insertion device to spread the gap 192 in the reinforcing guide wider, while simultaneously translating the reinforcing guide distally. As the gap 192 opening on the reinforcing guide 170 approaches the transition point between the two side walls 316 and the tubular portion 308 of the insertion tool 300, the gap 192 of the reinforcing guide is about as wide as the outside diameter of the tubular portion, which is larger than the diameter of the guide sheath 304. As the reinforcing guide 170 continues to be translated distally passed the tubular portion 308 of the insertion device 300, the reinforcing guide may be positioned onto the guide sheath 304.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. The catheter sheath comprising:
   an elongate tube having a proximal end, a distal end and a lumen therebetween;
   at least one weakened area in a non-longitudinal pattern along the length of the tube; and
   a tab coupled to the proximal end of the catheter sheath, the tab having at least one weakened area.

2. The catheter sheath of claim 1, wherein:
   the number of weakened areas on the tab is equal to the number of weakened areas on the sheath; and
   the weakened areas on the tab are aligned with the weakened areas on the sheath.

3. The catheter sheath of claim 1, wherein the tab comprises an annular shape having an outer diameter which is larger than the outer diameter of the sheath and an inner diameter which is substantially the same diameter as the diameter of the lumen in the sheath.

4. The catheter sheath of claim 1, wherein the at least one weakened area of the tab comprises a notch.

5. The catheter sheath of claim 1, wherein the at least one weakened area of the tab comprises a groove.

6. The catheter sheath of claim 1, wherein the at least one weakened area of the tab comprises a slit.

7. The catheter sheath comprising:
   an elongate tube having a proximal end, a distal end and a lumen therebetween;
   at least one weakened area in a non-longitudinal pattern along the length of the tube; and
   fins which project radially from the catheter sheath and run longitudinally along the catheter sheath, the fins being positioned at a proximal portion of the catheter sheath and about 90° apart circumferentially from the at least one weakened area in the tab.

8. A catheter sheath, comprising:
   an elongate tube having a proximal end, a distal end and a lumen therebetween;
   two weakened areas in a helical pattern along the length of the tube, the two weakened areas positioned substantially diametrically opposite each other;
   a tab coupled to the proximal end of the catheter sheath, the tab including an annular shape having an outer diameter which is larger than the outer diameter of the tube and an inner diameter which is substantially the same diameter as the diameter of the lumen in the tube, the tab having two weakened areas which are aligned with the weakened areas on the tube; and
   two fins positioned at a proximal portion of the tube and about 90° apart circumferentially from the at least one weakened area in the tube.

* * * * *